(12) United States Patent
Hanaoka

(10) Patent No.: US 6,730,211 B2
(45) Date of Patent: May 4, 2004

(54) AQUEOUS ELECTROLYZED SOLUTION OF ASCORBYL GLUCOSAMINE AND PREPARATION PROCESS THEREFOR

(75) Inventor: Kokichi Hanaoka, 1041, Oaza-Ueda, Ueda-shi, Nagano 386-0001 (JP)

(73) Assignees: Mikuni Corporation, Tokyo (JP); Kokichi Hanaoka, Nagano (JP)

( * ) Notice: Subject to any disclaimer, the term of this patent is extended or adjusted under 35 U.S.C. 154(b) by 205 days.

(21) Appl. No.: 10/114,603

(22) Filed: Apr. 2, 2002

(65) Prior Publication Data

US 2002/0179455 A1 Dec. 5, 2002

(30) Foreign Application Priority Data

Apr. 10, 2001 (JP) ........................................ 2001-110885

(51) Int. Cl.[7] .............................................. C01F 1/461
(52) U.S. Cl. ........................................ 205/413; 205/746
(58) Field of Search .................................. 205/413, 746

(56) References Cited

U.S. PATENT DOCUMENTS

| 5,736,027 A | 4/1998 | Nakamura | 205/742 |
| 6,551,492 B2 * | 4/2003 | Hanaoka | 205/742 |
| 2002/0027079 A1 | 3/2002 | Hanaoka | 205/50 |

FOREIGN PATENT DOCUMENTS

| JP | 05-059498 | * | 9/1994 |
| JP | 2001-347269 | * | 12/2001 |

* cited by examiner

*Primary Examiner*—Arun S. Phasge
(74) *Attorney, Agent, or Firm*—Norris McLaughlin & Marcus

(57) ABSTRACT

This invention discloses an aqueous cathodic electrolyzed solution of ascorbyl glucosamine exhibiting a lower oxidation-reduction potential than that in an aqueous solution of ascorbyl glucosamine in which a concentration of water-soluble inorganic salts is less than 0.1 M prepared by electrolyzing the starting ascorbyl glucosamine solution as well as a preparation process therefor. A concentration of ascorbyl glucosamine is 0.1 to 3 wt %. A current density in electrolysis is preferably 0.003 to 0.03 $A/cm^2$.

7 Claims, 4 Drawing Sheets

AQUEOUS ELECTROLYZED SOLUTION OF ASCORBYL GLUCOSAMINE AND PREPARATION PROCESS THEREFOR

BACKGROUND OF THE INVENTION

1. Field of the Invention

This invention relates to an aqueous electrolyzed solution prepared by electrolysis of a starting aqueous solution of ascorbyl glucosamine, which has a lower oxidation-reduction potential than the starting aqueous solution of ascorbyl glucosamine, as well as a preparation process therefor.

2. Description of the Related Art

It is a well-known technique that a dilute starting aqueous solution of an electrolyte (e.g., an alkali-metal chloride) as an electrolysis aid is electrolyzed in an electrolytic cell while removing an aqueous anodic electrolyzed solution with a lower pH generated around the anode (acidic water), which is then utilized for sterilization or disinfection (JP-A 6-246272). The electrolytic cell internally comprises inactive electrodes made of, e.g., platinum or a platinum alloy separated by a septum. The septum used is a charged membrane which is an ion-exchange resin film or a non-charged membrane having a microporous structure.

The aqueous anodic electrolyzed solution formed around the anode contains hypochlorous acid. Potent oxidizing and chlorinating action of hypochlorous acid has been widely utilized for sterilization or disinfection in medical institutions. In addition, since a small amount of ozone and/or dissolved oxygen in the acidic water can promote granulation, the acidic water has been studied for its use as an aid in surgical treatment.

An aqueous cathodic electrolyzed solution formed around the cathode (alkali water) may be also prepared by electrolyzing tap water in place of a dilute aqueous solution of an electrolyte and has been, for example, used for drinking.

It is also known technique that the above aqueous electrolyte solution comprising an organic acid such as ascorbic acid or gallic acid as an additive rather than as an electrolysis aid is electrolyzed (U.S. Pat. No. 5,736,027).

In the above process, ascorbic acid is used in the presence of an electrolysis aid. Ascorbic acid is added for controlling pH of the aqueous cathodic electrolyzed solution and removing free chlorine in the aqueous anodic electrolyzed solution.

Ascorbic acid (also called as vitamin C) is widely contained in fruits, vegetables or other foods. Particularly, antioxidative effect of ascorbic acid has been recently paid attention and thus ascorbic acid has been added to a product such as health foods and cosmetics for endowing these with the effect.

Antioxidative effect of ascorbic acid has been generally recognized since its disproportionation effect on superoxide anion radical which is a kind of radical (conversion of superoxide anion radical into hydrogen peroxide) was reported. Since Friedvich found superoxide dismutase (SOD), an enzyme capable of disproportionating superoxide anion radical, in 1869, antioxidating effect of ascorbic acid has been much more paid attention.

We have already filed a patent application based on an invention related to a process for preparing an aqueous anodic electrolyzed solution using ascorbic acid itself as an electrolysis aid (P 2001-347269A JAPAN).

Since ascorbic acid is extremely susceptible to oxidation, it is believed that keeping its quality stable is difficult. In particular, ascorbic acid in an aqueous solution is oxidized while being spontaneously decomposed. It cannot, therefore, stably exist for a long period. Furthermore, in an aqueous solution containing much dissolved oxygen, ascorbic acid is spontaneously decomposed into an oxidized form of ascorbic acid for a short time and thus lose its antioxidating effect. In preparation of an aqueous electrolyzed solution using ascorbic acid as an electrolysis aid, there is, therefore, a problem that an aqueous ascorbic-acid solution as a starting aqueous electrolysis solution cannot be stably stored for a long time.

We have made various attempts for solving the above problems and thus have hit an idea of using ascorbyl glucosamine as an electrolysis aid. Ascorbyl glucosamine has a complex in which ascorbic acid is surrounded glucosamine, and the structure allows ascorbic acid to have antioxidating effect. As a result, ascorbyl glucosamine can exhibit stable antioxidating effect.

In the fields of medical drugs, cosmetics and foods, decomposition of ascorbic acid in an aqueous solution has been prevented by any of known methods; for example, retardation of spontaneous oxidation of ascorbic acid by adding an antioxidant such as vitamin E and gallic acid. Examples of a stable form of ascorbic acid include ascorbyl palmitate prepared by reaction of a palmitate with ascorbic acid.

Since ascorbyl glucosamine is soluble in water and exhibits higher permeability to a skin, it has been utilized for skin care including cosmetics. In addition, ascorbyl glucosamine can suppress collagenase activity inhibiting collagen formation. Ascorbyl glucosamine has been, therefore, utilized in the field of cosmetics as an extremely effective promoter for forming collagen.

We have not found any report in which ascorbyl glucosamine is used as an electrolysis aid.

SUMMARY OF THE INVENTION

Thus, an objective of this invention is to provide a stable aqueous electrolyzed solution of ascorbyl glucosamine and a preparation process therefor.

To achieve the above objective, this invention provides:

[1] an aqueous cathodic electrolyzed solution of ascorbyl glucosamine exhibiting a lower oxidation-reduction potential than that in a starting aqueous solution of ascorbyl glucosamine in which a concentration of water-soluble inorganic salts is less than 0.1 M;

[2] the aqueous cathodic electrolyzed solution as described in [1] wherein a concentration of ascorbyl glucosamine is 0.1 to 3 wt % in the aqueous cathodic electrolyzed solution of ascorbyl glucosamine;

[3] the aqueous cathodic electrolyzed solution as described in [1] wherein the amount of dissolved oxygen is 0.2 to 0.5 mg/l in the aqueous cathodic electrolyzed solution;

[4] the aqueous cathodic electrolyzed solution as described in [1] exhibiting a lower oxidation-reduction potential by 100 mV or more than that in the starting aqueous solution of ascorbyl glucosamine;

[5] a process for preparing an aqueous cathodic electrolyzed solution of ascorbyl glucosamine comprising the step of electrolyzing a starting aqueous solution of ascorbyl glucosamine in which a concentration of water-soluble inorganic salts is less than 0.1 M to removing from the cathode side an aqueous electrolyzed solution of ascorbyl glucosamine exhibiting a lower oxidation-reduction potential than that in the starting aqueous solution of ascorbyl glucosamine;

[6] the process for preparing an aqueous cathodic electrolyzed solution as described in [5] wherein a concentration of ascorbyl glucosamine is 0.1 to 3 wt % in the starting aqueous solution of ascorbyl glucosamine;

[7] the process for preparing an aqueous cathodic electrolyzed solution as described in [5] wherein a current density in electrolysis is 0.003 to 0.03 A/cm$^2$.

According to this invention, the starting aqueous electrolysis solution is stable to oxidation because the starting aqueous solution is prepared using ascorbyl glucosamine, an ascorbic-acid derivative, as an electrolysis aid. An aqueous cathodic electrolyzed solution obtained is also stable to oxidation. The aqueous cathodic electrolyzed solution obtained is also extremely highly reductive. According to this invention, ascorbyl glucosamine having excellent anti-oxidating effect can be electrolyzed to provide an aqueous cathodic electrolyzed solution containing highly active dissolved hydrogen. The aqueous electrolyzed solution can be applied to a skin to exhibit excellent effects such as prevention or repair of oxidative skin damage.

In these figures, the symbols denote the following meanings; 2: starting aqueous electrolysis solution tank, 4: starting aqueous electrolysis solution, 6: pump, 8: supply line for a starting aqueous electrolysis solution, 10: electrolytic cell, 12: anode, 14: cathode, 16: septum, 18: anode chamber, 20: cathode chamber, 22: electrolysis power supply, 24: discharge line for an aqueous anodic electrolyzed solution, and 26: discharge line for an aqueous cathodic electrolyzed solution.

DETAILED DESCRIPTION OF PREFERRED EMBODIMENTS

Generally, when an aqueous electrolyte solution is electrolyzed while feeding the aqueous electrolyte solution between a pair of inactive electrodes separated by a septum, there is formed in the anode side an aqueous anodic electrolyzed solution having a lower pH, containing more dissolved oxygen and exhibiting a higher oxidation-reduction potential as an oxidation-reduction parameter than the aqueous electrolyte solution. Alternatively, an equivalent aqueous electrolyzed solution can be prepared by electrolysis without a septum under the condition that the electrolyte solution is fed as a stable laminar flow.

On the other hand, in the cathode side is formed an aqueous cathodic electrolyzed solution having a higher pH, containing more dissolved hydrogen and exhibiting a lower oxidation-reduction potential.

That is, electrolysis of an aqueous electrolyte solution can provide two aqueous solutions with different properties. Electrolysis of a monovalent-monovalent electrolyte such as sodium chloride forms hydrochloric acid, chlorine gas and dissolved oxygen in the anode side by an electrode reaction. Chlorine gas is dissolved in water to generate hypochlorous acid. Thus, pH is reduced as hydrochloric acid is formed.

In the cathode side, sodium ion and hydroxyl ion form sodium hydroxide, leading to increase in pH. Furthermore, dissolved hydrogen is generated by an electrode reaction.

In the process of this invention, ascorbyl glucosamine is used as an electrolysis aid without using any other electrolyte as an electrolysis aid. Electrolysis of a starting aqueous solution of ascorbyl glucosamine as an electrolyte provides an aqueous cathodic electrolyzed solution of ascorbyl glucosamine in the cathode side, which has become particularly highly reductive.

FIGS. 1(A) and 1(B) show a molecular structure and a molecular model for glucosamine, respectively.

Figure 1:
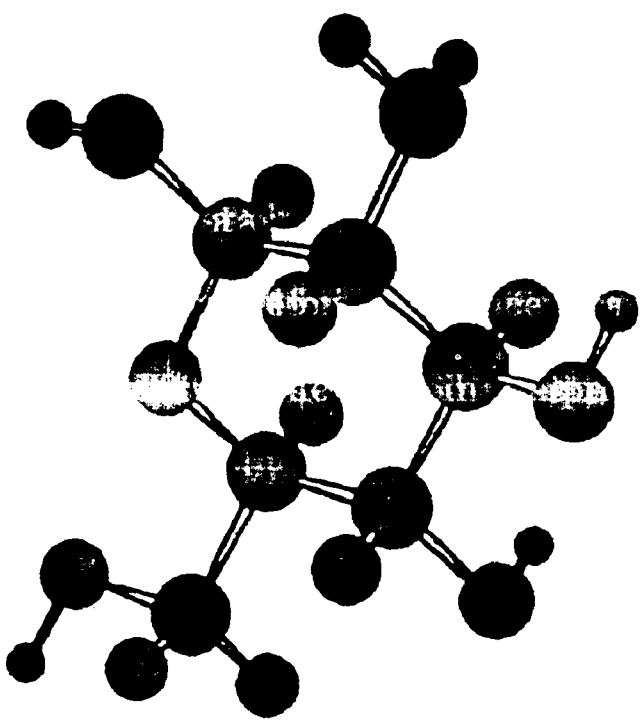
FIGS. 1(A) and 1(B) show a molecular structure and a molecular model of glucosamine, respectively.
Figure 1:
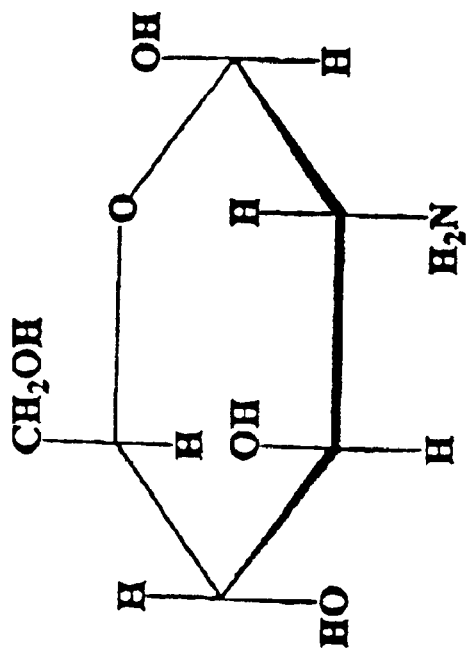

Ascorbyl glucosamine is a complex having a conformation where ascorbic acid is surrounded by a glucosamine polymer as shown in FIG. 1.

Figure 2:
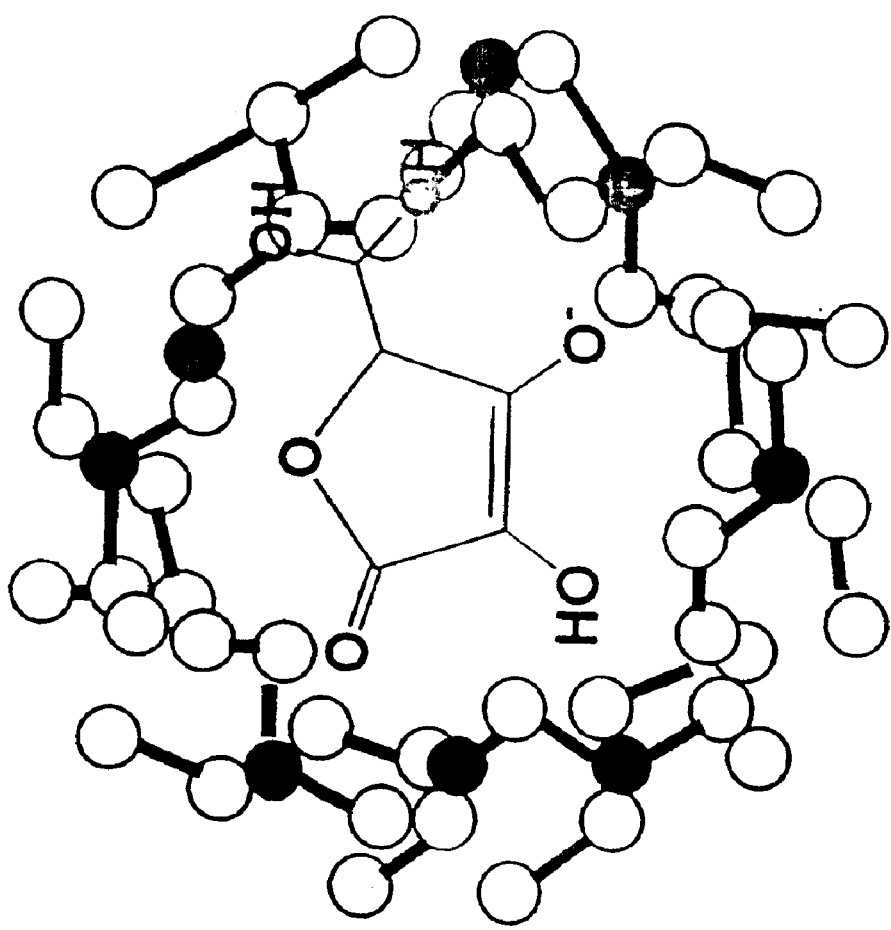
FIG. 2 is a conceptual diagram showing a conformation of ascorbyl glucosamine.

FIG. 2 conceptually illustrates the conformation of ascorbyl glucosamine. Ascorbyl glucosamine is a kind of complex having a positive charge derived from the nitrogen atom in the amino group in the glucosamine molecule and a negative charge derived from ascorbic acid, and is slightly ionized in an aqueous solution.

It can be, therefore, involved in electrolysis as a charged compound. When an electric field is applied to the aqueous solution, positively charged polyglucosamine in ascorbyl glucosamine is attracted to the cathode side while negatively charged ascorbic acid is attracted to the anode side.

In addition, in the anode and the cathode, the following electrode reactions of water occur so that hydrogen ion and oxygen gas are generated in the anode side while hydroxyl ion and hydrogen gas are generated in the cathode side.

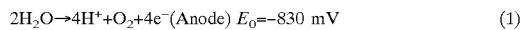
$$2H_2O \rightarrow 4H^+ + O_2 + 4e^- \text{ (Anode) } E_0 = -830 \text{ mV} \tag{1}$$

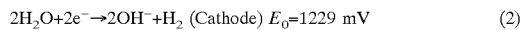
$$2H_2O + 2e^- \rightarrow 2OH^- + H_2 \text{ (Cathode) } E_0 = 1229 \text{ mV} \tag{2}$$

Thus, in comparison with a starting aqueous solution, pH is reduced and dissolved oxygen increases in the anode side while pH increases and dissolved oxygen is reduced in the cathode side.

Since pure water is essentially non-conductive, it is difficult to electrolyze pure water. Ascorbyl glucosamine used as an electrolysis aid in this invention is slightly ionized in an aqueous solution and thus acts as an electrolyte to allow water as a solvent to be involved in electrolysis.

Ionization level of ascorbyl glucosamine is, however, very low so that its solution has a relatively higher electric resistance. It is, therefore, believed that an electric field can move small amounts of glucosamine and ascorbic acid. Thus, majority of ascorbyl glucosamine exists with being unchanged.

On the other hand, in the above electrolysis, current-carrying effect of ascorbyl glucosamine causes electrode reactions of water, which is electrolyzed as illustrated in formulas (1) and (2). As a result, part of hydroxyl ion generated reacts with glucosamine to slightly increase pH and dissolved hydrogen gas reduces an oxidation-reduction potential in the cathode side. The oxidation-reduction potential E can be estimated using Nernst's equation described below:

$$E = E_0 - 0.0591(m/n)\text{pH} + (0.0591/n)\ln [OX]/[\text{Red}] \tag{3}$$

wherein $E_0$, OX and Red represent a standard oxidation-reduction potential, an oxidized form and a reduced form, respectively; and m and n represent coefficients in the terms in equation (4).

$$[OX] + mH^+ + ne^- \rightarrow [Red] \quad (4)$$

From equations (1), (2) and (3), an oxidation-reduction potential of the aqueous cathodic electrolyzed solution can be estimated as follows $$E = E_0 - 0.118\text{pH} + 0.0148 \log [O_2] - 0.0295 \log [H_2] \quad (5)$$

An oxidation-reduction potential depends on the concentrations of dissolved oxygen and dissolved hydrogen. Therefore, when pH and the concentration of dissolved oxygen are constant, the oxidation-reduction potential is univocally defined by the concentration of dissolved hydrogen.

In this invention, a slight level of ionization of ascorbyl glucosamine can be utilized for electrolysis of water to prepare an aqueous electrolyzed solution enriched with dissolved hydrogen. Dissolved hydrogen generated by electrolysis of water has a small average size as a molecular assembly so that it can exhibit great reductive effect. An oxidation-reduction potential is an indication for a level of oxidation and reduction. Of course, the lower an oxidation-reduction potential is, the higher reducibility is. Between aqueous solutions of ascorbyl glucosamine, reducibility can be, therefore, evaluated by comparing their oxidation-reduction potentials.

This invention will be described in detail with reference to the drawings.

There are no restrictions to an electrolyzer used for preparing an aqueous cathodic electrolyzed solution of ascorbyl glucosamine of this invention, and any conventional apparatus for preparing an aqueous electrolyzed solution can be used. Specifically, any type of apparatus can be used regardless of factors such as the size of the electrolyzer and presence of a septum in the electrolytic cell.

Figure 3:
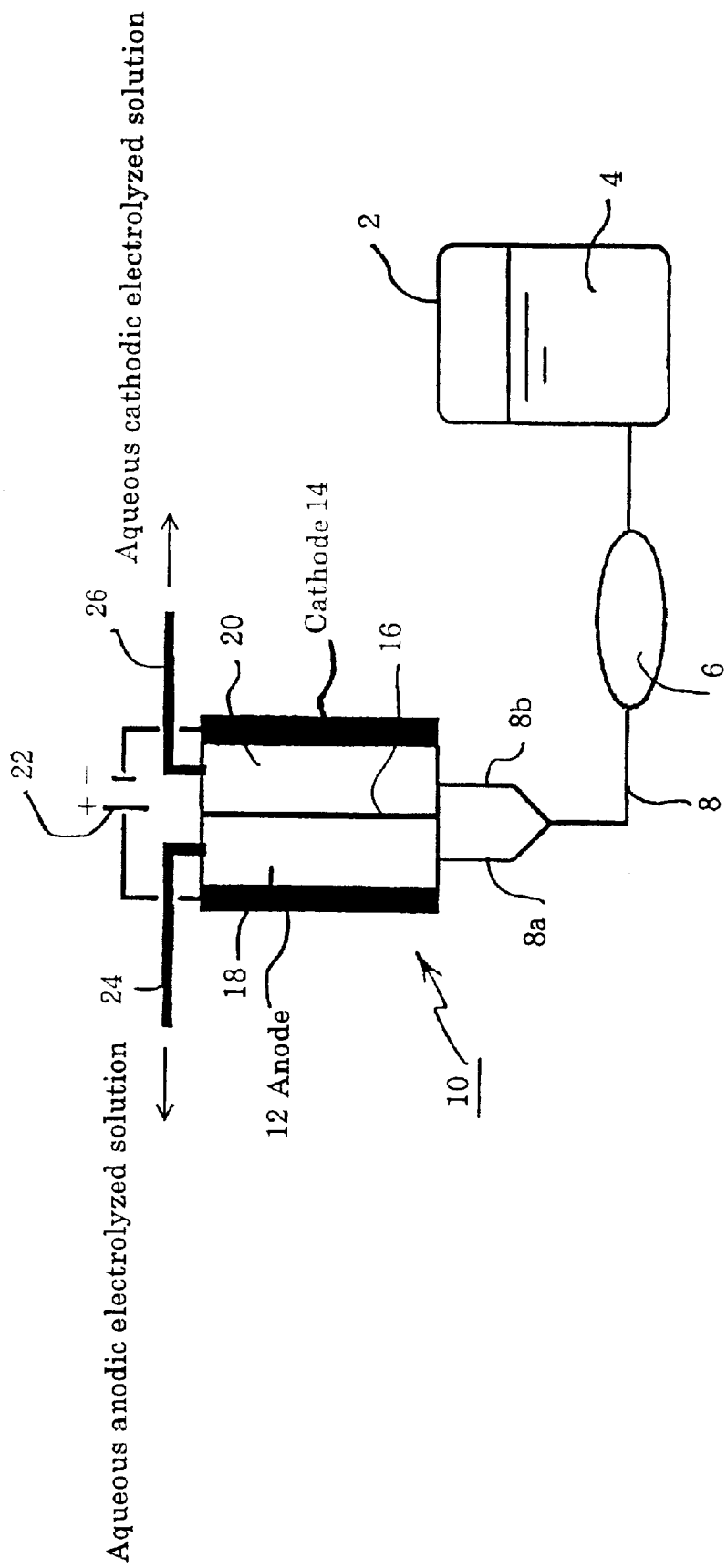
FIG. 3 is a schematic view showing an exemplary apparatus for preparing an aqueous cathodic electrolyzed solution according to this invention.

FIG. 3 is a schematic view showing an embodiment of an electrolyzer used for preparing an aqueous cathodic electrolyzed solution of this invention.

In FIG. 3, 2 denotes a starting aqueous electrolysis tank, which is filled with a starting aqueous electrolysis solution 4.

The starting aqueous electrolysis solution 4 contains 0.1 to 3 wt %, preferably 0.5 to 2 wt % of ascorbyl glucosamine. If the concentration of ascorbyl glucosamine is less than 0.1 wt %, a conductivity may be too low to electrolyze the starting solution. If it is more than 3 wt %, stickiness may be significant when the aqueous electrolyzed solution is applied on, e.g., a skin and thus it may be inappropriate depending on an application.

The starting aqueous electrolysis solution 4 desirably contains substantially no water-soluble inorganic electrolytes other than ascorbyl glucosamine. Examples of a water-soluble inorganic electrolyte include a variety of inorganic salts such as sodium chloride, potassium chloride, sodium sulfate, calcium chloride, ferric chloride, aluminum chloride and ammonium salts. The content of water-soluble inorganic electrolytes is preferably 0.1 mM or less in total, particularly preferably 0.02 mM or less.

As described above, an aqueous starting electrolysis solution can be prepared, for example, by dissolving ascorbyl glucosamine in purified water such as distilled water and deionized water to a concentration in the above range.

In this FIG., 6 denotes a pump connected to the apparatus via a supply line 8 for a starting aqueous solution, and the pump 6 can be operated to feed the starting solution 4 through the supply line 8 to the electrolytic cell 10.

The electrolytic cell 10 comprises an anode 12 and a cathode 14 separated from each other at a given distance and a septum 16 between and apart from these electrodes. Within the electrolytic cell 10, there are an anode chamber 18 delimited by the anode 12 and the septum 16 and a cathode chamber 20 delimited by the cathode 14 and the septum 16.

The anode 12 and the cathode 14 are made of an electrochemically inactive metal material; preferably, platinum or a platinum alloy.

The septum 16 prevents the aqueous anodic electrolyzed solution in the anode chamber 18 from being mixed with the aqueous cathodic electrolyzed solution in the cathode chamber 14. The septum is made of a material which is conductive to an electrolysis current. The septum may be selected from those conventionally used as an electrolysis septum such as an ion-exchange film and an uncharged film as appropriate.

The supply line 8 is branched upstream of the electrolytic cell 10 into branch lines 8a and 8b, which are connected to the anode chamber 18 and the cathode chamber 20, respectively.

In this FIG., 22 is an electrolysis power supply, in which a positive and a negative terminals are connected to the anode 12 and the cathode 14, respectively.

The aqueous electrolysis solution fed into the anode chamber 18 and the cathode chamber 20 via the above branch lines 8a and 8b, respectively, undergoes electrolysis. An electrolysis current density is preferably 0.003 to 0.03 A/cm$^2$, more preferably 0.01 to 0.02 A/cm$^2$. If an electrolysis current density is less than 0.003 A/cm$^2$, the amount of dissolved hydrogen in the aqueous cathodic electrolyzed solution discharged from the cathode chamber cannot be higher than that in the starting aqueous electrolysis solution. An electrolysis current density more than 0.03 A/cm$^2$ may be uneconomical because dissolved hydrogen in the aqueous cathodic electrolyzed solution may not be increased in proportion to increase in a current.

Therefore, an electrolysis current density may be controlled within the above range to adjust dissolved hydrogen in the aqueous cathodic electrolyzed solution discharged from the cathode chamber to a higher concentration than that in the starting aqueous electrolysis solution, preferably 0.2 to 0.5 mg/L, more preferably 0.3 to 0.4 mg/L.

The aqueous anodic electrolyzed solution thus formed is discharged from a discharge line for an aqueous anodic electrolyzed solution 24 while the aqueous cathodic electrolyzed solution is discharged from a discharge line for an aqueous cathodic electrolyzed solution 26.

In the above description, this invention has been described in reference to an electrolytic cell 10 within which a septum is disposed, but this invention is not limited to the specific configuration and an electrolytic cell without a septum may be suitably used.

Such an electrolytic cell without a septum may have, for example, a structure where an anode plate and a cathode plate are closely placed without a septum between them and electrolysis is conducted while a starting aqueous electrolysis solution is continuously fed between the cathode and anode plates and an aqueous anodic electrolyzed solution formed around the anode surface is continuously removed from a point downward to the anode; for example, an electrolytic cell disclosed in JP-A 6-246272. An aqueous cathodic electrolyzed solution can be removed by reversing electrode polarity.

In this invention, a starting aqueous solution may be electrolyzed to provide an aqueous cathodic electrolyzed solution with a lower oxidation-reduction potential by 100 mV or more, preferably by 150 to 230 mV than the starting aqueous solution.

EXAMPLES

This invention will be more specifically described with reference to examples.

Example 1

An electrolyzer shown in FIG. 3 was used for electrolyzing a starting aqueous solution of ascorbyl glucosamine (AG). Within the electrolytic cell were placed in parallel electrodes made of titanium coated with platinum (20 mm×17 mm) separated from each other at a distance of 0.2 mm, which were used as an anode and a cathode. The electrolytic cell was a non-septum type. An internal volume of the electrolytic cell was 68 mm$^3$. While feeding a starting electrolysis solution into the electrolytic cell at a flow rate of 25 mL/min, electrolysis was conducted to provide an aqueous anodic and an aqueous cathodic electrolyzed solutions. A voltage was controlled to adjust an electrolysis current density to 0.03 A/cm$^2$.

The starting aqueous solution was prepared by adding ascorbyl glucosamine to deionized water to a concentration of 0.1 wt %. Since deionized water was used, the content of water-soluble inorganic salts in the starting solution was extremely small (less than 0.01 mM).

The aqueous cathodic electrolyzed solution thus formed after electrolysis was collected for determining pH, an oxidation-reduction potential (ORP) and the amount of dissolved oxygen (OD). The results are shown in Table 1. As a reference, ORP and DO measurement results for the starting solution before electrolysis are also shown in Table 1 (Reference Example 1).

TABLE 1

|  | PH | ORP (mV) | DO (mg/L) |
| --- | --- | --- | --- |
| Example 1 | 3.94 | 47 | 7.2 |
| Reference Example 1 | 3.75 | 145 | 5.93 |

*ORPs are observed values for a reference electrode and DOs are measured values at 25° C.

Example 2

Electrolysis was conducted as described in Example 1, except that a concentration of ascorbyl glucosamine in a starting solution was 0.3 wt %. Measurement results of parameters such as pH for an aqueous cathodic electrolyzed solution obtained are shown in Table 2.

TABLE 2

| pH | ORP | DO |
| --- | --- | --- |
| 4.0 | −89 mV | 6.87 mg/L |

Example 3

Electrolysis was conducted as described in Example 1, except that a concentration of ascorbyl glucosamine in a starting solution was 3 wt %. Measurement results of parameters such as pH for an aqueous cathodic electrolyzed solution obtained are shown in Table 3.

TABLE 3

| PH | ORP | DO |
| --- | --- | --- |
| 3.98 | 20 mV | 7.66 mg/L |

Comparative Example 1

Electrolysis was conducted as described in Example 1, except that a concentration of ascorbyl glucosamine in a starting solution was 0.05 wt %. A current density was as small as 0.005 A/cm$^2$ and thus electrolysis did not sufficiently proceed. Measurement results of parameters such as pH for an aqueous cathodic electrolyzed solution obtained are shown in Table 4.

TABLE 4

| PH | ORP | DO |
| --- | --- | --- |
| 3.75 | 140 mV | 6 mg/L |

Evaluation Test 1

The aqueous cathodic electrolyzed solution obtained in Example 2 was used for a sensory evaluation in terms of skin care.

For comparison, a 50 mM aqueous solution of ascorbic acid (AsA) was electrolyzed using the apparatus described in Example 1 at a current density of 0.01 A/cm$^2$ to obtain an aqueous anodic electrolyzed solution, which was then used for a sensory evaluation.

A test protocol was as follows.

1) Subject: 14 healthy women who tend to have rough skin;
2) Test procedure: an aqueous anodic electrolyzed solution of ascorbic acid was applied to 7 of 14 subjects while an aqueous cathodic electrolyzed solution of ascorbyl glucosamine was applied to the remaining seven subjects. A test period was 21 days and a sample was applied to face and hands. The number of subjects in whom each tested effect was observed was converted into a percentage. Table 5 shows the results.

TABLE 5

|  | AsA electrolyzed aq. | AG electrolyzed aq. |
| --- | --- | --- |
| Irritation | 0% | 0% |
| Moisture retention | 84 | 91 |
| Refreshment | 100 | 100 |
| Smell | 0 | 100 |
| Whitening | 46 | 83 |
| Improvement in rough skin | 85 | 90 |

Stability Study

The following study was conducted for evaluating oxidation stability of ascorbyl glucosamine. One of methods for evaluating oxidation stability is determination of the amount of dissolved oxygen. In an aqueous solution, ascorbic acid consumes dissolved oxygen to be converted from a reduced form to an oxidized form. Therefore, stability of ascorbic acid to oxidation can be estimated from a reduced amount of dissolved oxygen.

Figure 4:
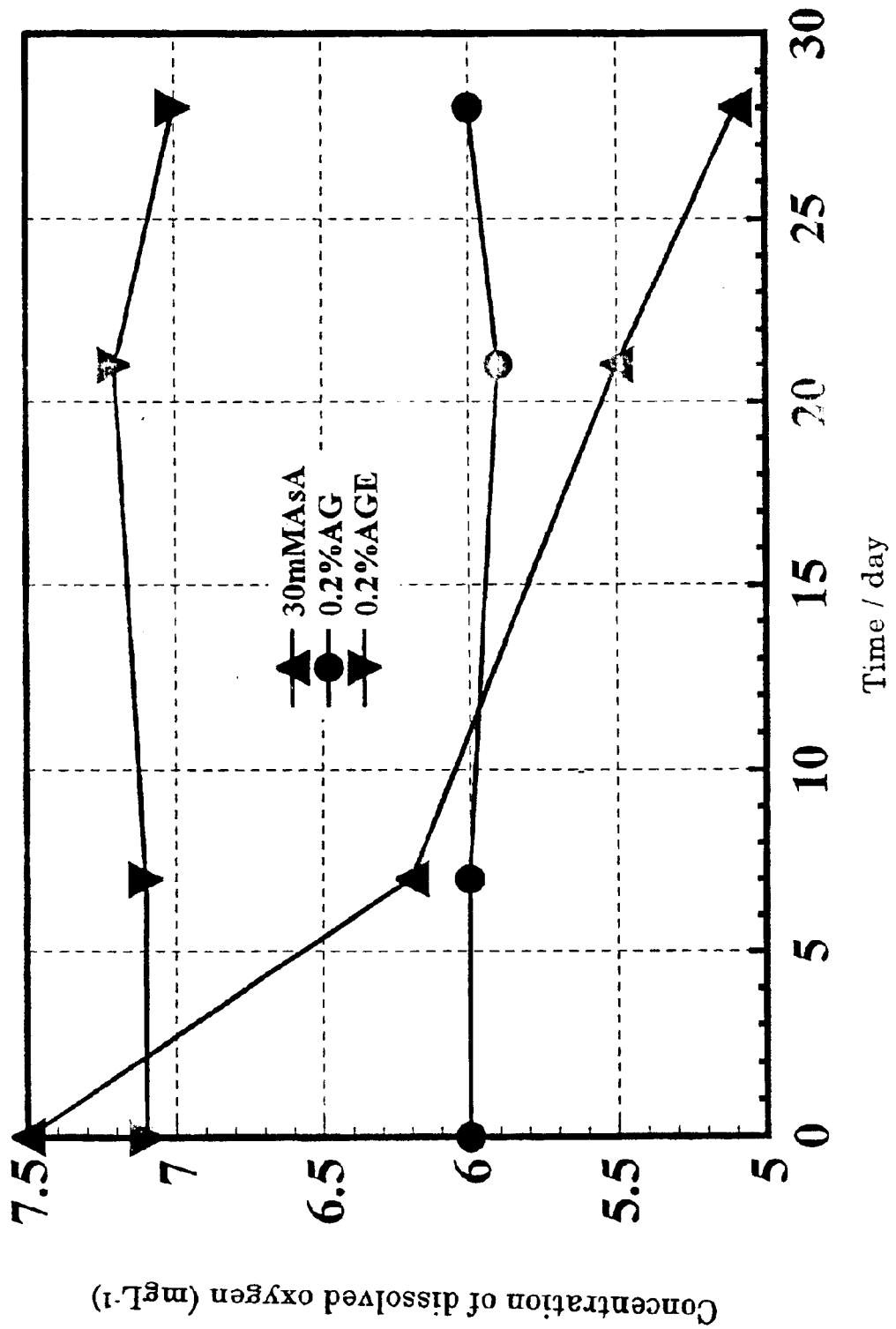
FIG. 4 is a graph showing investigation results for oxidation stability of ascorbic acid and ascorbyl glucosamine.

In a closed system, 30 mM ascorbic acid (30 mM AsA), 0.2 wt % ascorbyl glucosamine (0.2 wt % AG) and a 0.2 wt % aqueous cathodic electrolyzed solution of ascorbyl glucosamine were stored at an ambient temperature, and for these samples, dissolved oxygen contents were determined on 7, 21 and 28 days. The results are shown in FIG. 4.

In 30 mM aqueous ascorbic acid solution, a content of dissolved oxygen was reduced with time, indicating that ascorbic acid is susceptive to oxidation.

A content of dissolved oxygen was substantially unchanged during 28 days in 0.2 wt % ascorbyl glucosamine and the aqueous cathodic electrolyzed solution of ascorbyl glucosamine, indicating that ascorbyl glucosamine in an aqueous ascorbyl glucosamine solution or an aqueous cathodic electrolyzed solution of ascorbyl glucosamine is insusceptible, i.e., stable, to oxidation.

What is claimed is:

1. An aqueous cathodic electrolyzed solution of ascorbyl glucosamine exhibiting a lower oxidation-reduction potential than that in a starting aqueous solution of ascorbyl glucosamine in which a concentration of water-soluble inorganic salts is less than 0.1 M.

2. The aqueous cathodic electrolyzed solution as claimed in claim 1 wherein a concentration of ascorbyl glucosamine is 0.1 to 3 wt % in the aqueous cathodic electrolyzed solution of ascorbyl glucosamine.

3. The aqueous cathodic electrolyzed solution as claimed in claim 1 wherein the amount of dissolved oxygen is 0.2 to 0.5 mg/l in the aqueous cathodic electrolyzed solution.

4. The aqueous cathodic electrolyzed solution as claimed in claim 1 exhibiting a lower oxidation-reduction potential by 100 mV or more than that in the starting aqueous solution of ascorbyl glucosamine.

5. A process for preparing an aqueous cathodic electrolyzed solution of ascorbyl glucosamine comprising the step of electrolyzing a starting aqueous solution of ascorbyl glucosamine in which a concentration of water-soluble inorganic salts is less than 0.1 M to removing from the cathode side an aqueous electrolyzed solution of ascorbyl glucosamine exhibiting a lower oxidation-reduction potential than that in the starting aqueous solution of ascorbyl glucosamine.

6. The process for preparing an aqueous cathodic electrolyzed solution as claimed in claim 5 wherein a concentration of ascorbyl glucosamine is 0.1 to 3 wt % in the starting aqueous solution of ascorbyl glucosamine.

7. The process for preparing an aqueous cathodic electrolyzed solution as claimed in claim 5 wherein a current density in electrolysis is 0.003 to 0.03 A/cm$^2$.

* * * * *